United States Patent [19]

Gargione

[11] 4,168,783

[45] Sep. 25, 1979

[54] INTRAVENOUS BOTTLE HOLDER

[75] Inventor: Frank V. Gargione, Absecon Highlands, N.J.

[73] Assignee: Wheaton Industries, Millville, N.J.

[21] Appl. No.: 795,202

[22] Filed: May 9, 1977

[51] Int. Cl.² .................. B65D 23/12; A61J 1/00; A61M 5/14

[52] U.S. Cl. .................. 215/100 R; 128/272; 128/214 R

[58] Field of Search ............... 128/272, 214.2, 214 R, 128/227, 213, 215; 248/311.3, 318; 222/181, 185; 215/100 R, 100 A; 206/806

[56] References Cited

U.S. PATENT DOCUMENTS

| 2,635,604 | 4/1953 | Fredrickson | 128/272 |
|---|---|---|---|
| 3,278,216 | 10/1966 | Hidding | 215/100 A |
| 3,307,752 | 3/1967 | Anderson | 215/100 A |
| 3,381,838 | 5/1968 | McClain | 215/100 A |
| 3,402,910 | 9/1968 | Purvis | 248/318 |
| 3,594,891 | 7/1971 | Cunningham | 215/100 A |
| 3,635,367 | 1/1972 | Morita | 248/311.3 |
| 3,744,658 | 7/1973 | Fujio | 215/100 A |
| 3,807,679 | 4/1974 | Burke | 215/100 A |
| 3,948,404 | 4/1976 | Collins | 215/12 R |
| 4,022,416 | 5/1977 | Kaye | 248/318 |

Primary Examiner—Robert W. Michell
Assistant Examiner—Arthur S. Rose
Attorney, Agent, or Firm—Miller & Prestia

[57] ABSTRACT

An intravenous bottle holder providing support of the bottle when the bottle is shipped or stored in its upright position, and providing a means for securely hanging the bottle in inverted position during its use, is provided. The bottle holder comprises an integral molded structure including a disc member having an opening therein, a pleated bail member spanning the opening, and an annular skirt depending from one disc side formed with an annular snap ring on the inside skirt portion so that the holder can be demountably attached to a desired bottle.

5 Claims, 4 Drawing Figures

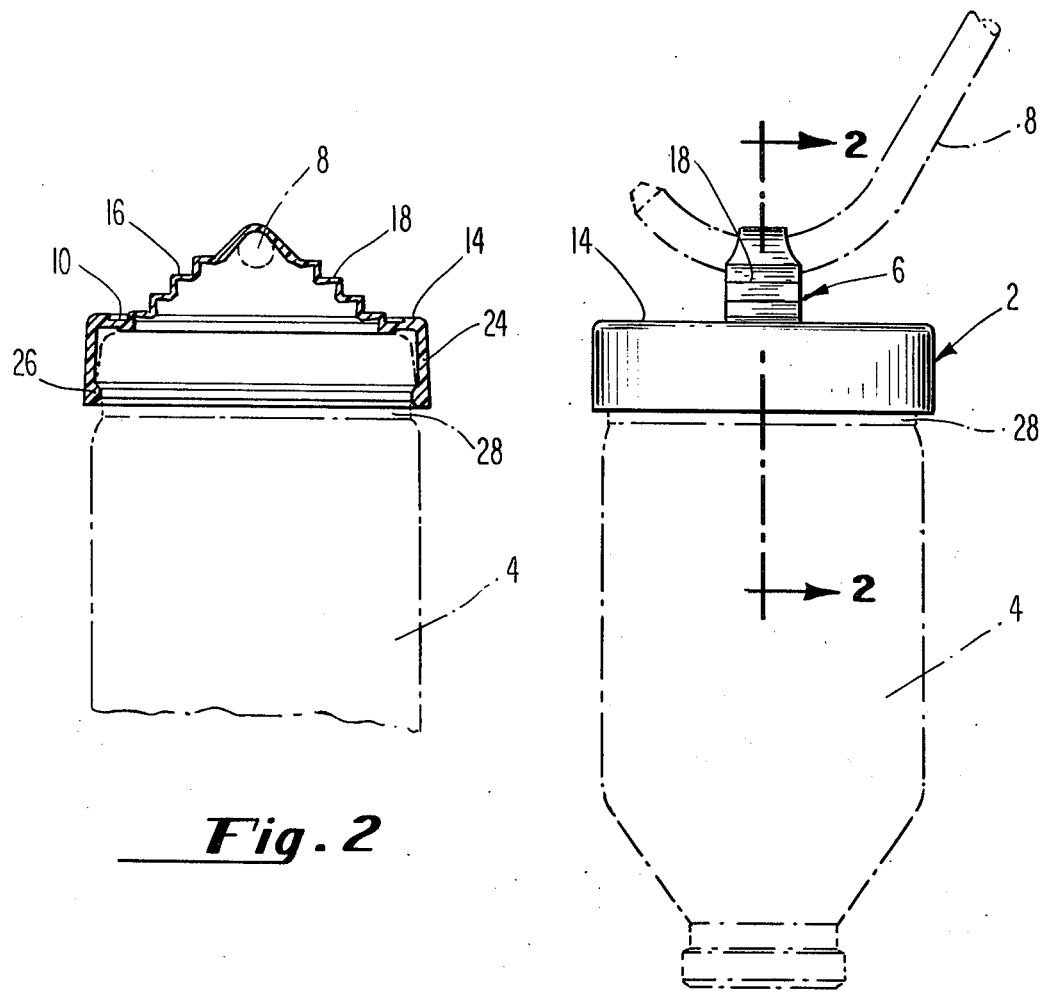
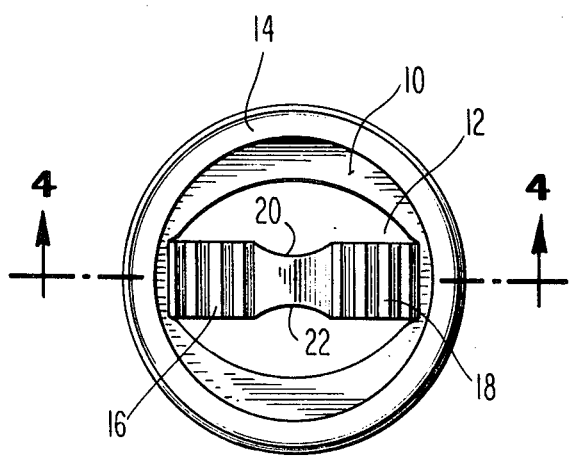
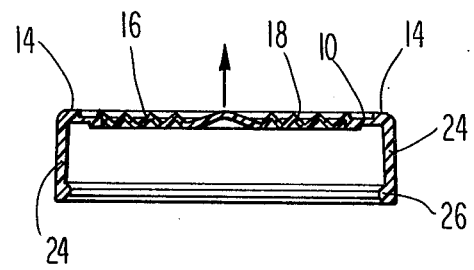

INTRAVENOUS BOTTLE HOLDER

BACKGROUND OF THE INVENTION

1. Field of the Invention

This invention relates to a bottle holder of the type providing support and protection for the bottle when the bottle is stored or shipped in its upright position and also providing a hanging means so that the bottle may be hung in inverted position during its use.

2. Description of the Prior Art

Intravenous feed bottles must be hung on metal hooks of an intravenous feed pole when in use providing the patient with his food supply. Also, the bottles themselves must be protected against damage when the bottles are shipped or stored in their upright position.

Many attempts have been made to provide an intravenous bottle holder that both protects the bottle during shipment and storage and includes a means for hanging the bottle in inverted position during its use.

Several prior art bottle holders have been referred to in the prior art statement under 37 C.F.R. 1.97 concurrently filed herewith.

However, these prior art holders fail to provide an inexpensive holder member that allows the bottle to be safely positioned in the upright position so that the bottle will not tilt or wobble due to the bail or hanging strap member disposition under the bottom surface.

Also, many of the prior art holders do not provide a sure attachment of holder to bottle so that the risk of the bottle separating from the holder and crashing to the floor during inverted hanging of the bottle is always present.

Accordingly, it is an object of the present invention to provide an inexpensive intravenous bottle holder that will provide an even support, without tilt or wobble caused by the hanging strap attachment on the bottle's bottom side.

Further, it is a more specific object to provide an intravenous bottle holder that provides a sure attachment of holder to bottle so that the risk of bottle breakage when the bottle is hung for use is minimized.

SUMMARY OF THE INVENTION

These and other objects are met by the present invention. Basically, the intravenous bottle holder comprises an integral thermoplastic molded structure; the thermoplastic blank usually being injection molded into shape. The holder is molded to include a disc section with an opening therein, a pleated bail spanning the opening, and an annular skirt depending from one disc side that includes an annular bead on the inside skirt portion serving as a snap ring to demountably detach the holder to a bottle.

The pleats in the bail provide a means for expanding the bail so that it may be attached to a desired arm or the like so that the bottle may be hung in inverted position.

Also, the pleated bail may be provided with a grasping section including two opposed concave face side surface members so that the user can readily grap the bail and hang it on the desired structure.

Also, the disc may include an integral annular support rim protruding from the disc side opposite the annular skirt. The rim surrounds the opening and acts as a support member for the bottle-holder assembly to prevent bottle tilting or wobbling when the bottle is stored or shipped in its upright position.

When the bottle is hung in its inverted position, the vertical force applied to the bail by the intravenous feed pole hook is transformed, due to the integral thermoplastic holder construction, into a horizontal force, biasing the snap ring inwardly to firmly grasp the bottle.

The invention will be easily understood when the following detailed description is read in conjunction with the attached drawings.

BRIEF DESCRIPTION OF THE DRAWINGS

In the drawings:

FIG. 1 is a side elevational view of the holder and bottle in inverted hanging position;

FIG. 2 is a sectional view taken on plane 2—2 of FIG. 1;

FIG. 3 is a plan view of the holder; and

FIG. 4 is a sectional view of the holder taken on plane 4—4 of FIG. 3.

DETAILED DESCRIPTION OF THE PREFERRED EMBODIMENT

With reference to the drawings and especially to FIG. 1 there is shown holder 2 composed of a thermoplastic material, attached to intravenous feed bottle 4. Bail 6 provides a means for hanging the bottle to a desired hanging arm structure shown at 8.

As seen in FIGS. 3 and 4, the integral molded plastic structure includes an annular disc member 10 formed with an opening 12 therein. Annular support rim 14 surrounds the opening, and protrudes from the disc so that the bottle may be supported thereon when the bottle is placed in its upright position.

Bail 6 is attached to opposite sides of the disc, and spans the opening. Bail 6 includes pleated sections 16, 18, and a grasping section composed of two opposed concave faced surface members 20, 22. The grasping section is disposed intermediate the pleated sections.

The pleated bail sections allow the bail to be expanded when grasped so that the bottle may be hung by inserting a hanging arm or the like through the loop defined by the bail. See FIG. 1.

The bail, when folded in its flat configuration, is disposed totally within opening 12 and within the plane formed by rim 14 so that the bottle will not wobble or tilt when attached to the holder and disposed in its upright position.

As can be seen in FIG. 4, the holder includes annular skirt 24 depending from the disc side opposite the support rim. The interior skirt side is provided with annular bead 26 that serves as a snap ring so that the holder can be demountably attached to bottle 4.

As best seen in FIG. 1, the bottle is provided with annular recess 28 located toward the bottom bottle portion. Annular bead 26 snap fits into recess 28 to provide a sure grip of holder to bottle.

When the bottle is hung in its inverted position, the vertical force exerted on bail 6 is transformed, due to the integral thermoplastic construction of the holder, into a horizontally oriented force, biasing annular bead 26 inwardly to securely engage bottle recess 28. Accordingly, a safe grip of holder to bottle is assured.

The holder in accordance with the invention is preferably injection molded, and composed of polypropylene.

It will be apparent to those skilled in the art that many variations and modifications of the present invention can be made. Such variations and modifications are clearly within the ambit of the appended claims.

I claim:

1. A bottle holder for an intravenous feed bottle, the holder including:
   (a) a disc having an opening therein;
   (b) a pleated bail integral with the disc and spanning the opening;
   (c) a resilient annular skirt integral with the disc and depending from one disc side, the inside portion of the skirt including an annular bead serving as a snap ring to demountably attach the holder to a bottle; and
   (d) an annular support rim integral with and protruding from the disc side opposite the skirt so that the bottle may be supported thereby when it is placed in upright position, the rim surrounding the opening, the bail, when folded in flat configuration, being totally disposed within the opening and within a plane formed by the rim.

2. A bottle holder as recited in claim 1 further including a substantially planar grasping section located intermediate pleated sections of the bail.

3. A bottle holder as recited in claim 2 wherein the grasping section includes two opposed concave face side surface members.

4. A bottle holder as recited in claim 1 wherein the holder is composed of polypropylene.

5. A bottle holder as recited in claim 1 in combination with an intravenous feed bottle, the bottle having an annular recess formed around the bottom portion to form a snap fit with the holder bead.